United States Patent [19]
Raam

[11] Patent Number: 6,162,606
[45] Date of Patent: *Dec. 19, 2000

[54] IMMUNOHISTOCHEMICAL METHOD FOR THE DETECTION OF DEFECTIVE ESTROGEN RECEPTORS

[75] Inventor: Shanthi Raam, 872 Oak Hill Ave., Attleboro, Mass. 02703

[73] Assignee: Shanthi Raam, Rehoboth, Mass.

[*] Notice: This patent is subject to a terminal disclaimer.

[21] Appl. No.: 08/432,577

[22] Filed: May 1, 1995

Related U.S. Application Data

[63] Continuation-in-part of application No. 08/051,619, Apr. 22, 1993, abandoned.

[51] Int. Cl.$^7$ .................................................. G01N 33/53
[52] U.S. Cl. ........................... 435/7.1; 435/7.23; 436/501; 436/519; 436/548; 436/63; 436/64; 436/813; 530/388.22; 530/388.24
[58] Field of Search ..................................... 435/7.1, 7.23, 435/7.8, 960; 436/501, 519, 548, 63, 64, 813; 530/388.22, 388.24

[56] References Cited

U.S. PATENT DOCUMENTS

| | | | |
|---|---|---|---|
| 4,215,102 | 7/1980 | Lee ............................................... | 424/3 |
| 4,711,856 | 12/1987 | Spelsberg ................................. | 436/504 |
| 4,873,313 | 10/1989 | Crawford et al. ....................... | 530/387 |
| 5,084,380 | 1/1992 | Carney ................................... | 435/7.23 |

OTHER PUBLICATIONS

Tamura, H., Raam, S. et al, Eur J Cancer and Clin. Onc., 20, 1261–1277, 1984.
Raam, S. et al, Eur J Cancer and Clin. Onc. 18: 1–12, 1982.
Ram, S. et al, J Natl Cancer Inst., 80: 756–67, 1988.
Robert NJ et al, Breast Cancer Res Treat., 16: 273–278, 1990.
Raam, S. Editor/Author, Immunology of Steroid Hormone Receptors, vol. 1; Publisher: CRC Press, Boca Raton, FL, 1988, table of contents and pp. 62–65.
Raam, S. and H. Tamura: Abstract in: Proc. AACR: 1991.
Raam, S. and H. Tamura: Abstract in: Proc. Endocrince Soc., 1991.
King RJB et al, Breast Cancer Res. Treat., 2: 336–342, 1982.
Ludwig, L. et al, Mol. Endocrinology, 4: 1027–1033, 1990.
Dotzlaw, H. et al, Mol. Endocrinology, 6: 773–785, 1992.
Nomura Y et al, J Natl Cancer Inst., 82: 1146–1149, 1990.
Blaustein JD et al, Endocrinology, 132: 1218–24, 1993.
Marx J. Editorial Science, 257: 744–5, 1992.
Nigg EA et al, Cell, 66: 15–22, 1991.
Raam S et al, Breast Dis 3: 127–130, 1990.
Schwartzman G and Workman P, Eur J Cancer 29 A: 3–14, 1993.
Smith PJ et al, Cancer Research, 52: 4000–4008, 1992.
Kessel D et al, Cancer Research, 51: 4665–4670, 1991.
Raam. S. et al., Eur. J. Cancer and Clin. Onc., 18:1–12, 1982.
Raam. S. et al., Molecular Immunol., 18: 143–156, 1981.
Raam. S. et al., Breast Cancer Res. Treat; 3: 179–199 1983.
Richardson. S. et al., Glyncologic Onlology, 17: 213–230, 1984.
Tamura H., Raam S., et al., Eur. J. Cancer and Clin. Onc., 20: 1261–1277 (1984).
Raam. S. et al., J. Natl. Cancer. Inst., 80: 756–761, 1988.
Robert. NJ. et al., Breast Cancer Res. Treat., 16: 273–278, 1990.
King R.J.B et al., Breast Cancer Res. Treat., 2: 339–346, 1982.
Ludwig, L. et al., Mol. Endocrinol., 4: 1027–1033, 1990.
Dotzlaw. H. et al., Mol. Endocrinol., 6: 773–785, 1992.
Fugua . S. et al., Cancer Res., 51: 105–109, 1991.
King, W.J., et al., Cancer. Res., 45: 293–304, 1985.
Blaustein J.D. et al., Endocrinol, 131: 1336–1342 (1992).
Chamness G.C. et al., J. Histochem. Cytochem., 28: 792.798 (1980).
Raam. S. et al., Proc. XI International Congress of Clinical Chemistry, 499–505, (1982)., Editiors: E. Kaiser, F. Gabl, M.M.Müller, M. Boyer Publisher: Walter de Gruyter & Co., New York, Berlin.
Hamburger A.W and Salmon S.E., Science, 197: 461–463, 1977.
Schwartzman. G. and Workman P., Eur. J. Cancer 29A:3–14, 1993.
Nomura et al., J. Natl. Cancer Inst. 82: 1146–1149, 1990.
S. Raam, H. Tamura (Abstract) #1291: Proc. AACR, 32: Mar. 1991.
S. Raam, H. Tamura (Abstract) #593: Proc. Endocrine Society, May 1991.

(List continued on next page.)

*Primary Examiner*—Geetha P. Bansal

[57] ABSTRACT

Identification of defective ER and subclassifying ER+ breast cancers on the basis of the presence of defective ER is described as a tool potentially useful, as previously shown by the results of a pilot study, for predicting which among the ER+ tumors will respond and which will fail to repsond to hormonal modes of therapy. Improvements are introduced in the specimen sampling and ligand introduction steps of the immunohistochemical procedure which was developed for sub-classifying estrogen receptor-positive tumors of human breast cancers and other cancers of the estrogen target organs on the basis of the presence of defective estrogen receptors. Additionally, a new monoclonal antibody reagent which has potential use as a replacement for the polyclonal anti-ER antibody reagents is also described. The modified steps include the use of tumor imprints instead of cryosections; use of ligand coated slides instead of the original ligand layering step. Both these modifications which simplified the execution of the test procedure and the availability of a suitable monoclonal antibody reagent should facilitate wider use and automation of the entire procedure if needed. Methodology for the application of this modified test procedure for rapidly screening drug compounds to detect which affect the translocation behaviour of defective ER and as a simple tool for identifying the presence of components in water and other solutions which might be toxic to the normal non-defective estrogen receptors found in normal tissues are also presented.

7 Claims, No Drawings

OTHER PUBLICATIONS

Marx.J. Editorial, Science, 257: 744–745, 1992.

Raam S. Editor/Author, Immunology of Steroid Hormone Receptors, vol. 1: Immunology of Estrogen Receptors: Publisher CRC Press, Boca Raton, Fla, 1988.

S. Raam and H. Tamura (Abstract) Presented at the 1815 New England Endocrine Conference, Oct. 13, 1980.

Blaustein J.D. Endocrinology 132: 1218–1224, 1993.

Nigg E.A et al., Cell 66: 15–22, 1991.

Raam S. et al., Breast Dis. 3: 127–130, 1990.

Smith P.J. et al. Cancer Research, 52: 4000–4008, 1992.

Kessel D. et al., Cancer Research, 51: 4665–4670, 1992.

Harlow et al 1988 p. 372 Chapter 10. In Antibodies "A Laboratory Manual" Ed. Harlow and Lane Cold Spring Harbor Lab (1988).

IMMUNOHISTOCHEMICAL METHOD FOR THE DETECTION OF DEFECTIVE ESTROGEN RECEPTORS

This application is a continuation-in-part of application Ser. No. 08/051,619, filed Apr. 22, 1993, now abandoned.

FIELD OF INVENTION

This invention pertains to an automatable cytological, immuno-histochemical procedure which was developed for studying the intracellular movement of estrogen receptors (ER) found in cancer cells. Among cancers, in addition to ER which required specific ligand binding to induce its translocation from cytoplasm to the nucleus (normal variety), two defective varieties of ER were present. Tumors with abnormal ER were found to predominate among hormone therapy-resistant breast cancers. Therefore, the potential use of this test is to predict which among ER+ tumors will respond to and which will be resitant to hormone therpay.

Also of concern is the alternative use of this immunohistochemical procedure, for identifying in a malignant cell, normal and abnormal compartmentalization of kinetic biological components other than steroid hormone receptors, which similar to the steroid hormone receptors, exert their biological function by moving from one location of the cell to another, either in response to the binding of a specific ligand or to phosphorylation or a combination of both.

Also of concern is the alternative use of this immunohistochemical procedure as a first level drug screening procedure, and to customise selection for each tumor, those drugs which are able to inhibit or alter the abnormal compartmentalization of a kinetic cellular substance encountered in malignant cells.

Also of concern is the alternative application of this immuno-histochemical procedure as a first level toxin screening procedure, to identify toxins present in the ingested food, either ingested or injected pharmaceutical drugs, or toxins found in drinking water, which have the capacity to induce abnormal compartmentalization of kinetic cellular components.

Also of concern is the alternative use of this immunohistochemical procedure as a hybridoma screening procedure, to screen the hybridomas that are known to secrete anti-kinetic substance antibodies, to select those which secrete antibodies that specifically interact with and bind to normal varieties of kinetic substance only, to abnormal varieties only, or to both normal and abnormal varieties of that kinetic cellular substance.

For postmenopausal women diagnosed of estrogen receptor positive (ER+) breast cancer, hormonal mode of therapy is still the preferred mode of treatment. Of 180,000 new cases of breast cancer detected annually, 70% are expected to be ER+ and one half of these will also possess progesterone receptors (PR). Despite the advance of new methods and discovery of new marker proteins, hormone therapy failures among ER+ cases amount to 50%. Presence of hormone receptors as such, does not guarentee clinical response of the tumor to hormone therapy. Thus, there is a dire need for a test to predict with better precision than currently possible, which among the ER+ tumors will and which will not respond to hormone therapy. Such a test should also be adaptable to very small malignant lesions which are being detected by mammography. In addition, there is also an urgent need for identifying new drugs to treat hormone resistant cancers. An automatable drug screening test is also needed to allow a rapid selection of potential candidate drugs from a large variety of drug compounds.

This invention report relates to the development of an immuno-histochemical test which is useful for identifying three subclasses among ER+ tumors, one subclass characterized by the presence of normal ER and two subclasses which contain ER which are defective in their ability to translocate from the cytoplasmic to the nuclear compartment.

With the use of the immunohistochemical procedure originally published in 1984, 1988 and 1990, subclassification of ER+ tumors was done by appying polyclonal anti-ER-antibodies to detect the cellular location of ER in cryosections of cancers. A pilot study on the correlation of such a subclassification of ER+ tumors with clinical response to hormonal therapy also revealed that tumors with normal ER are responsive to hormone therapy, while those with defective ER fail to respond. With such an encouraging preliminary data, it was important to devise a test which is suitable for wider use so that significance of the observations of the pilot study can be evaluated via large multicentric clinical studies and "bench to the bed side" transition of this technology is made feasible. The test must therefore be easy to perform and automatable. Monoclonal anti-ER antibody reagents with special features which can be used in place of the polyclonal anti-ER antibodies are also essential. This invention describes such an immunohistochemical test with an automatable steps and teaches procedural details to obtain simultaneous identification of normal and defective translocation of ER. The same test is also useful for pilot screening of drugs. The same technique also served as an useful tool to select among the hybridomas, those which secrete broad spectrum monoclonal antibodies with characteristics essential to merit their use for immunohistochemical subclassification of receptor positive tumors.

With the advent of genetic engineering technology, several proteins which execute their function by moving from one compartment of the cell to another are being identified. The importance of defining the specific chromosome to which a nuclear binding protein binds in normal versus malignant cell is emphasised for understanding the onset of malignancy. It is becoming increasingly important to identify which transcription factor interacts with which messenger RNA to regulate the transcription and to detect abnormalities in that transcription process. The immunohistochemical test described in this invention allows the identification of any kinetic component in a cell, which executes its biological function by moving from one compartment of the cell to another and the detection of abnormalities in the kinetic function which are often found in malignancy. A broad spectrum antibody specific to the kinetic protein is required.

DESCRIPTION OF PRIOR ART

A: Detection of normal and abnormal nuclear translocation of ER

An immunohistochemical method (1), was originally developed for identifying ER found in human breast cancers. For this method, polyclonal antibodies (2) which specifically bind to ER present in human breast cancer biopsies (1,2) were reacted with ER present in cryosections of cancer biopsies. Detection of the cellular location of ER bound by the antibody was done by a procedure known to prior art as indirect immunofluorescent test (also known as sandwich technique), which employs fluorescein tagged secondary antibodies which bind to the anti-receptor antibodies (1). At this time, a method to fix (immobilize) the ER protein in its own cellular compartment was also described. This procedure, termed "gradual ethanol dehydration-rehydration procedure" is described in several publications (1,3,4,5 ). The dehydration steps consist of 10 minute exposure of the four micron thin cryosections of tumors to each of the saline solutions containing increasing concentrations of ethanol : 30, 50, 75 or 90 percent ethanol in 0.9% Sodium Chloride solution, followed by absolute ethanol and xylene. The exposure of the tissue to gradually increasing concentrations of ethanol was found to be mandatory to preserve the ER in its own cellular compartment, and in an antibody reactive form (1). This dehydration step was followed by rehydration step which was the reversal of the dehydrating steps using a fresh set of saline solutions containing 90, 75, 50, or 30 % ethanol. The cryosections are then washed three times in plain saline solution to remove all the residual ethanol before the rabbit anti-ER antiserum is layered onto the sections and allowed to react with cellular ER for 30 minutes. The serum proteins and the excess unbound anti-ER antibodies is removed by washing the sections in saline and the fluorescein tagged secondary antibodies are allowed to react with the sections for 30 minutes. The sections are washed clean of excess secondary antibodies, mounted with coverslips and the location of immunofluorescence was identified using UV microscope. The immuno-histochemical technique was adopted subsequently to study the estrogen-dependent nuclear binding of ER, known to those skilled in art as "in-vitro translocation" of ER. Estrogen receptors which are present in the cytoplasmic compartment of the cells capture their specific ligand estrogen and undergo conformational change which enables the estrogen complexed ER to bind to specific sites in the cell nucleus. Estrogen receptors like the other steroid hormone receptors are kinetic proteins because they move from one compartment of the cell to the other upon binding to their specific ligand. In a normal cell, the translocation of these kinetic proteins are induced by their specific ligands and all the cellular events or gene transcriptions which occur posterior to the binding of the ligand are termed ligand dependent events. In malignant cells or diseased cells however abnormalities related to this event of translocation often occur.

Translocation of ER was first examined in cells derived from normal human endometrium and grown in tissue culture (3). Either a saline solution, or saline containing nanomolar concentrations of estrogen which is the natural ligand for ER, called estrogenic ligand, or Diethylstilbesterol (DES), also known to those skilled in prior art to be an estrogenic ligand, or a compound which is not recognised as a ligand by ER (eg: R5020 or ORG 2058 which are progesterone analogs which bind to progesterone receptors), termed a control ligand, are added to the growth medium in which the endometrial cells are grown. After two hours the cells are fixed by ethanol dehydration-rehydration method in order to obtain an in-situ fixation of ER as they exist in the cell. The ER in the fixed cells were examined by indirect immunofluorescent technique and the results revealed that the ER was found in the cytoplasm in those cells which were incubated with either plain saline or control ligand in the growth medium. The ER in the endometrial cells which were in medium containing estrogen or DES however were found exclusively in the nucleus (3).

The malignant endometrial cells ("KLE" cells ) and malignant breast cancer cells (MCF-7 cells) similarly examined by the immunohistochemical procedure, revealed the presence of ER which were abnormal. In the malignant KLE cells, and in approximately 30–40% of MCF-7 cells, ER was unable to translocate to the nucleus even when estrogen was present in the medium and these abnormal ER were capable of binding estrogen as verified by radioligand technique (3,4). Therefore, the defect was related to the nuclear binding function of ER. Another abnormality of ER was also noted in approximately 10% of MCF-7 cells. The ER was found to be located in the nuclei even in the absence of estrogen in the medium (3). However, the majority of MCF-7 cells (60%) contained ER which were normal in relation to their nuclear binding function and in these cells, as found in normal endometrial cells, ER had to first complex with estrogen before it translocated and bound to the nucleus (3).

The immunohistochemical procedure (1, 3 ) was further improved to render it suitable for examining the nuclear binding properties of ER present in the breast cancer biopsy specimens (5). Breast biopsies are normally stored frozen at −80C in order to preserve the ER and other steroid hormone receptors functionally intact. Therefore, the immunohistochemical procedure was made suitable for studying ER in cryosections. This improvement consisted of an addition of a ligand incubation step (5) prior to fixing the cryosections by ethanol dehydration rehydration technique (1). The cryosections, in duplicates, were either processed without any ligand, or were exposed for 30 minutes, in a moist chamber at 37° C., either to a saline solution of estrogen, DES, or control ligand ORG 2058. Thirty microliters of one of the ligand solutions were layered on to the air-dried cryosections and immediately, most of the solution were aspirated leaving just a thin film of the ligand solution on the cryosections. The ligand overlay step is crucial for determining the translocation abnormalities of ER and the reproducibility of this procedure was verified by testing the same tumors several times and by including an ER+ tumor with transolcating variety of ER, as a positive control, every time an unknown sample is evaluated (5,6).

Several primary biopsies of breast cancers from postmenopausal women, determined to be ER+ by biochemical radioligand procedures had excess tissue which had been cryopreserved at −80C. These tumors were evaluated by immunohistochemical nuclear binding test, for the nuclear binding properties of their ER (5,6). As found among cells in culture, three varieties of ER were found in breast cancer biopsies. The tumors were classified according to the compartmentalization of antibody specific fluorescent staining (exclusively Cytoplasmic, C+N−; Cytoplasmic and Nuclear C+N+; Nuclear only, C−N+) and on the basis of percentage of tumor cells showing those patterns of staining in the presence versus absence of estrogenic ligand.

Interpretation of results obtained in ER+ tumors from postmenopausal women and criteria for determining ER defects are detailed in prior art publications (6, 7). Briefly, the classification criteria were as follows:

TR+L Non-defective: ER is able to bind to the nucleus only in the presence of estrogen or DES . This is because ER must complex with its specific ligand for aquiring the conformation that enables it to bind to the cell nucleus. A tumor is classified as TR+L, when the staining pattern is C+N− in the absence of estrogen or DES, but in the presence of these ligands, the staining pattern changes to C+N+ or C−N+ in >30% of cells.

TR(−) Defective: ER is unable to bind to the nucleus. A tumor is classified as TR(−) if the staining pattern is C+N− in ≧70% of the tumor cells both in the absence and in the presence of estrogen or DES.

TR+NL Defective: ER, although able to bind estrogen, does not require estrogen binding step to transform and bind to the nucleus. Nuclear binding occurs in the absence of specific ligand. Tumors are classified as TR+NL if the staining pattern in the absence or presence of estrogen or DES, is either C+N+ or C−N+, in ≧30% of tumor cells.

The reproducibility of the staining pattern and the quality of antibody reagents and the drug solutions were verified by several criteria as detailed in prior publication (6). These measures are the following:

1. Quality of the reagents were verified by including an ER+ tumor of TR+L or TR+NL variety as a known positive control. Reproducibility of the classification of these tumors served as criterion for reagent quality.
2. Since the percentage of tumors were quantified manually by at least two independent investigators skilled in art, the inter-assessor variability in classifying the tumors was evaluated by comparing their results on overall classification of tumors and percent tumor cells recorded as having the staining pattern specified for that sub-class ( TR+L, TR+NL or TR−). Correlation was found to be in excess of 90% (6). In cases where there was discrepancy between the investigators in the value of percentage of cells, an average of the values was used to determine the sub-group.

Among 88 cases so studied, complete details of clinical response were also available for 25 women who had recurrences and were treated by hormone therapy. A pilot correlative study was performed to assess the clinical significance of subclassifying ER+ tumors on the basis of the results of the immunohistochemical test (6,7). The subclassification data on 88 ER+tumors and clinical response of 25 cases among these tumors when subjected to hormone therapy are given in Table I. These data are taken from two prior publications (6,7).

TABLE 1

CLINICAL SIGNIFICANCE OF SUBCLASSIFICATION OF ER+ TUMORS

|   | Incidence of ER sub-class in primary breast cancers N = 88 | | Clinical response to hormone therapy N = 25 | |
|---|---|---|---|---|
| 1. TR+L | (normal) | 31% | 5/6 | (83%) |
| 2. TR+NL | (abnormal) | 31% | 0/10 | ( 0%) |
| 3. TR(−) | (abnormal) | 38% | 3/9 | (33%) |

Statistical significance of the clinical response data was performed by two sided Fisher's exact test and found to be significant (p=0.011) as referenced in prior publication (7).

The immunohistochemical subclassification of the primary biopsies of ER+ tumors on the basis of nuclear binding characteristics of ER, as shown in the table was found to be of clinical significance. Primaries of TR+L variety showed the highest rate of clinical response to hormone therapy with 5 out of 6 patients showing response; none of the tumors of TR+NL variety responded; only three among nine TR− variety responded. The clinical features of these 25 patients, type and duration of hormone therapy, interval between initial diagnosis and detection of recurrence, the clinical outcome of response vs non-response, criteria for assessment of clinical response are all detailed in prior publication (referenced herein as 7).

It was also observed that immunohistochemical subclassification of ER+ tumors based on nuclear binding characteristics of ER served as a better predictor of clinical outcome to hormone therapy than progesterone receptor which is often used as a predictive marker. Tumors containing both ER and PR are considered to respond to hormone therapy with higher frequency than ER alone (8). For 17 patients among the 25 patients given in Table 1, PR status was known and therefore it was possible to compare the efficacy of PR status versus immunohistochemical subclassification based on nuclear binding defects of ER, to predict response to hormone therapy (7).

TABLE 2

(data taken from reference 7)

|  | Response | No effect | Progression | Total | % response |
|---|---|---|---|---|---|
| ER+/PR+ | 4 | 1 | 5 | 10 | 40% |
| ER+/PR− | 2 | 2 | 3 | 7 | 29% |
| TR+L | 5 | 0 | 0 | 5 | 100% |
| TR+NL | 0 | 2 | 8 | 10 | 8% |
| TR(−) | 1 | 1 | 0 | 2 |  |

As illustrated in Table 2, the nuclear binding defects in ER were independent of PR status of the tumor. This meant that some tumors with defective ER had PR in their tumor cells while some with normal ER were devoid of PR. In this pilot study subclassification of ER+ tumors on the basis of presence or absence of defective ER was found to be a better predictor of clinical outcome. Regardless of presence of PR, tumors with non-defective ER responded and all those with defective ER of TR+NL variety failed to respond. The number of TR(−) tumors with known PR status was insufficient for similar evaluation.

Several other procedures are available in the literature as prior art to study the nuclear binding of ER or other steroid hormone receptors. These are: a) Biochemical procedure described by Spelsburg T. C. (U.S. Pat. No. 4,711,856, dated Dec. 8, 1987)., b) Biochemical microtiter well nuclear binding assay described by Ludwig. L et al (9)., and c) Application of molecular genetics procedure for detection of mutant receptors described by Dotzlaw. H et al (10) or by Fuqua. S et al (11) for identifying DNA binding portion of ER molecule in ER negative but PR positive tumors.

d) Histochemical staining of steroid hormone receptors with the aid of hormones conjugated to fluorochrome tagged proteins as described by Lee. S. H et al (S. H. Lee, U.S. Pat. No. 4,215,102: dated Jul. 29, 1980);

e) Immunohistochemical staining procedures described for simple detection of ER and PR (ERICA and PRICA) as originally described by King W. J. et al for ER, which utilizes monoclonal anti-ER antibodies reactive with nuclear bound ER in the tissues (12) and f) Immunohistochemical staining of cancer tissues for ER and/or PR utilizing antibodies directed to specific sites in the ER or PR molecule as those described by Blaustein J. D (13).

Inherent disadvantages of biochemical procedures of detecting non-nuclear binding defective receptors are many. The tumor extracts are used as a source of receptors, but a standard non-tumor derived DNA preparation is employed for detecting DNA binding of receptors which are complexed with radio-labelled ligand. Use of extracts precludes the study of compartmentalization and the amount of tissue required is substantial and this feature renders these procedures unsuitable for small microscopic tumors often detected by mammography.

With none of the biochemical procedures available as prior art (9, 10, 11 and Spelsburg T. C: U.S. Pat. No.

4,711,856: Dec. 8, 1987) it is possible to distinguish between TR+L and TR+NL variety of receptors, primarily because only receptors completed with radiolabelled hormone are identified in these procedures.

Detection of mutant receptors with the aid of molecular probes and PCR amplification procedures (10,11) are multistep procedures which are not 6 conveniently automatable; additionally, these techniques are unsuitable for visualizing intracellular compartmentalization of receptors in individual tumor cells in response to inducers of intracellular translocation.

Histochemical procedure described by Lee S. H. et al (U.S. Pat. No. 4,215,102: Jul. 29, 1980 ) cannot differentiate among the high affinity binding of true ER or PR and other low affinity binders as shown by Chamness G. C. et al (14) and by Raam. S et al (15). More importantly, this procedure as described, cannot distinguish between TR+L and TR+NL varieties of ER or PR because it relies on detection of fluorochrome tagged ligands completed to these proteins. Ligand-independent translocation cannot therefore be defined by this detection procedure.

Immunohistochemical detection procedures described by King W. J. et al (12) and further researched by Blaustein J. D. et al (13) are also unsuitable for detection of defective ER or PR because the monoclonal antibodies used in this system are capable of identifying only nuclear bound receptors in all the specimens. According to Blaustein J. D. et al (13) these results are due to idiosyncratic behaviour of these antibodies. Immunohistochemical staining of receptors with site specific monoclonal antibodies or polyclonal antibodies were also found by Blaustein J. D. et al to yield results similar to those described by King W. J. et al (12). Site specific antibodies, monoclonal or polyclonal as described by Blaustein J. D. et al (13) were found unsuitable to demonstrate in vitro translocation of ER from the cytoplasm to the nucleus because of the inaccessibility of these antibodies ( H222, ER 715, ER 21 ) to that portion of the ER molecule which is unaffected by either ligand binding or nuclear binding by ER. Site specific antibodies are often prepared against a small segment of receptor molecule. This approach of raising antibodies ignores the biological, functional and structural impact of conformational specificity of that portion of the receptor as it exists in the intact protein. Post transcriptional modification of that portion of the receptor which occur in vivo are also absent in the synthetic polypeptides often used for producing site specific antibodies.

Thus, for studying intracellular kinetics of a cellular component, the specific antibodies should recognize ligand free, ligand bound, nuclear free, nuclear bound forms of that component. Only polyclonal anti ER antibody developed by Raam S. et al ( 2, 3, 5 and 6 ) and monoclonal antibody 1-F11 described as a part of this invention fulfill these criteria. Without such an antibody, whether polyclonal or monoclonal, simultaneous identification of normal and abnormal varieties of the kinetic component is not possible by immunodetection techniques.

B. Drug Screening Tests Available As Prior Art

Clonogenic Assay, in which the cancer cells are allowed to grow on agar in the presence or absence of drug compounds, is the most widely used screening system (16). Those drugs which fail to support the cloning and growth of cancer cells are selected for cancer treatment. This assay has been automated and adopted for customizing drugs to treat individual patients. This procedure of drug selection has following disadvantages:

Clonogenic assay system, similar to all available drug screening tests (17), is based on the effect of drugs on cell viability. A drug which is equally toxic to both normal and cancer cell are therefore liable to be selected.

This assay is not useful for selection of drugs which interact specifically with ER normal or abnormal, which are present in cancer cells.

This test requires several days to complete. Cell suspensions are prepared from the tumor biopsies with the use of proteolytic enzymes which are known to alter the surface properties of plasma membranes. Therefore drugs which are toxic to the enzyme treated cancer cells in vitro, are frequently ineffective in vivo when given to the cancer patient.

Preparation of viable single cell suspension from solid tumors is essential for success of this assay system but most difficult to achieve (16). Nomura et al (18) who applied this system to examine 534 breast cancers, report successful colony formation in only 276 biopsies.

This system is unsuitable for selection of drugs on the basis of specific interaction of drugs with kinetic proteins. Normal cells fail to grow on agar and therefore, this drug selection system cannot be adopted to study interaction of drugs with kinetic components found in normal cells, nor to compare the drug effect on a normal versus an abnormal kinetic component.

C: Currently Utilized Hybridoma Screening Procedures:

Culture supernates from hybridomas are generally screened for the presence of secreted antibody molecules, to distinguish the antibody secretors from non secretors. The next level of screening is performed to verify if those antibodies react with the antigen of interest. In this step, one discriminates those hybridomas which produce antibodies which are most specific to the antigen from those which secrete antibodies to irrelevent antigens. The third level of screening is performed to establish the monoclonality of the secreted antibody and for this purpose, the specific class and subgroup of secreted immunoglobulins (ie: antibody molecules) are defined. Only those hybridoma clones which secrete a single specific type of immunoglobulin are accepted as monoclonal.

Currently all the three level hybridoma screening is done by microplate Enzyme labelled Immunoassay system known to those skilled in art as ELISA test. In this assay system, the antigen is coated on to the microplate and the antibody in the culture supernate is allowed to react with the plate-bound antigen. The secondary antibodies labelled with an enzyme (either peroxidase or alkaline phosphatase) are then allowed to bind to the antigen-bound antibody molecules. If the antibodies which react with the plate bound antigen are present in the hybridoma supernates, positive color signal is obtained when the plate is developed for the presence of the enzyme label on the secondary antibody.

The ELISA assay is not suitable as described, nor can it be adopted for screening hybridomas to select those monoclonal antibodies to ER (or any kinetic component) which are able to react with either normal or abnormally compartmentalizing varieties of ER or those which show a broad reactivity to both abnormal and normal varieties. An immunohistochemical assay system such as the one described for studying ER translocation is needed for identifying antibodies with these features, primarily because a visualization of intracellular compartmentalization of the antigen in the presence or absence of the translocation inducers is relevant for the process of antibody selection.

SUMMARY OF THE INVENTION

Immunohistochemical procedures (3,5,6,7) which have been previously described for studying intracellular translocation of steroid hormone receptors utilize thin cyrosections and ligand layering steps which are not automatable. Additionally, during the process of making 4–5 micron thin cryosections from tumor biopsies, considerable tissue is wasted. Among microscopic breast cancer lesions detected by mammography or other cancers by similar X-ray technology, the amount of tumor tissue available for diagnstic and prognostic assays is limited. Furthermore, use of cryosections precludes the study of kinetic cellular components which are denatured by freezing. Since in a tumor, both normal and cancer cells are present together, cryosections or extracts of tumors are not the ideal choice as samples, when the object is to analyse the translocation features of hormone receptors or other kinetic components as they occur in cancer cells, without complications due to accompanying presence of normal cells. Unique features of the immunohistochemical procedure described in this invention are:

1. Use of imprints from frozen or fresh tumors;
2. Use of glass slides coated with ligand solutions, plain saline or control ligand solutions, omitting the non-automatable step of layering of ligand solutions;
3. Automation of tissue fixation step with the use of automatic slide processor VARISTAIN, purchased from Shandon InC.,
4. Its potential utility as a predictive test for predicting clinical outcome of the tumor when subjected to hormone therapy.
5. Utility as a hybridoma screening test. From several hybridomas secreting anti-ER antibodies, a hybridoma designated 1-F11 (20-F8-1-G7-1-F11; (19,20) was identified by this procedure and the anti-ER antibodies secreted by 1-F11 in turn has been used for the detection of normal and abnormal translocation of ER in cancers. By employing the procedure described in this invention, hybridoma screening was possible without any requirement for the use of purified normal ER or abnormally translocating ER as antigens in the assay system. Only paraffin sections or imprints of tumors known to contain normal or abnormal variety of ER are required as an antigen source. A very small volume of hybridoma culture fluid is sufficient to perform this test, hence it is very useful for situations in which a very limited quantity of assay material is available. The source of antigen is either the whole cell, tumor imprint, or smears from biological fluids without a need for extraction and purification of antigen.
6. Utility as a drug screening to identify drug compounds or toxins which alter the kinetic properties of abnormal or normal varieties of ER. With this method, simultaneously, individual tumors can be analysed for the type of ER present in the tumor (ie: normal or abnormal variety) and which drug compound is able to modify or inhibit abnormal translocation of ER present in that tumor. Following the same principles, those skilled in art should be able to identify drug compounds or toxins which alter the translocation of any kinetic protein. It is also important to identify which among the drugs that are given to patients as a part of combination chemotherapy, will inerfere with the normal translocation of ER and eliminate those drugs for that patient.

Advantages of using tumor imprints for immunohistochemistry:

This invention concerns the use of tumor imprints made on histological slides in place of cryosections. Imprints are made either from frozen or fresh unfrozen tumors. Tumor imprinted on glass is devoid of normal cells, stroma or connective tissue, because only cancer cells are transferred to the glass surface. Yet the pattern of tumor architecture is maintained in the imprint, because it is a replica of the tumor. During the imprinting process no tissue is wasted and even from microscopic lesions, several imprints can be made. When the tumor is large, by cutting a large tumor into smaller pieces and taking imprints of the cut surface of those pieces, areas most representative of the tumor mass can be selected for immunohistochemical test. A comparison of the translocation characteristics of a kinetic component in a normal tissue and cancer is also done with the procedure, when required, by comparing the intracellular location of the kinetic component in the presence or absence of specific inducer. The normal cells from body fluids are either smeared or cryosections of normal tissue thaw-mounted on glass slides, while cells from malignant fluids are smeared or imprinted from the tumors on to the glass slides.

Use of tumor imprints instead of clonogenic assay is ideal for drug screening for cancers, because the contamination from normal cells is avoided; the enzyme digestion step for preparation of single cell suspensions is eliminated; very little tumor tissue is required for making several imprints enabling customization of drugs for individual tumors; and imprints from fresh unfrozen tumors made on sterile glass slides, can also be grown in tissue culture in the presence or absence of the drug compound to be tested.

Advantages of using glass slides precoated with ligand or drug solutions:

Previously published immunohistochemical nuclear binding test (5–7) includes a step in which, the exposure of cryosections to ligands was achieved by layering the ligand solutions on top of cryosections in a specific manner so as to leave only a very thin film of the ligand solution on top of the cryosections. This delicate procedure was devised in order to prevent the loss of cytosolic receptors by solubilization during the ligand incubation and subsequent washing steps. The intricacy of this step and the skill needed to execute this step in a reproducible manner were quite significant, discouraging a wider use of this test procedure. Neither was it feasible to subject this layering step to automation.

In the described invention, the ligand layering step is ommitted. Instead, histological slides which are precoated with the ligand solutions or plain saline are used and imprints of tumors are directly made on those slides. If use of cryosections are mandatory, they can be thaw mounted directly on these slides. Smears of cells either in malignant or normal body fluids are also be made (as described in reference 5) directly on the ligand-coated slides. Use of ligand-coated slides for tumor imprints or cryosections ensures uniform exposure of all the attached cells to the ligand. Ligand Incubations are done in moisture chambers as described previously (5–7). Process of precoating of slides with ligand solution can be automated, for large scale studies.

Autoprocessing of the slides:

Shandon's VARISTAIN is an instrument which was developed for automation of histological staining procedure. In the described invention, this instrument's intended use is modified instead, to automate the tissue fixation by ethanol-dehydration-rehydration procedure (19,20). Therefore, instead of the staining solutions, the containers are filled with ethanol-saline mixtures, absolute ethanol, or xylene and the instrument is programmed to transfer the slides from one solution to another at specific time intervals. Use of VARISTAIN in this fashion for this immunohistochemical procedure, enables auto-processing of a large number of slides, a feature which makes this test attractive to a wider audience in clinical diagnostic laboratories, drug screening labs and suitable for commercial applications such as hybridoma screening.

DETAILED DESCRIPTION OF THE INVENTION

Definitions a) A kinetic biological component: refers to any cellular component which executes is biological function by moving from one location in the cell (site of origin or S.O) to another location (site of destination or S.D). and binding to that location. The process of movement is called translocation. The kinetic component can therefore be a protein, a polypeptide, a carbohydrate, a mucopolysaccharide, lipids or lipoproteins, nucleic acids, histones or non-histones, or components termed receptors.

b) Ligand: Specific ligands are those which upon binding to the normal kinetic component initiates the intracellular movement of that protein from S.O to its S.D. Control ligands are those which do not bind or initiate movement of the kinetic component. Ligands belong to the category of steroids hormones or non-steroid hormones, metals such as Iron, Molybdenum, Zinc, Calcium, Phosphorus, or polypeptides, histones, nonhistones, nucleic acids, polynucleotides, either naturally occuring in the cells or their synthetic analogs. Attachment or removal of phosphate groups also acts to trigger intracellular movement of a kinetic component (21).

c) Normal versus abnormal variety of translocation: Normal translocation is the pattern of translocation observed for the kinetic component found in the normal cell and is known to be crucial for the execution of its biological function. Abnormal varieties refer to any deviation from that normal pattern. Example: Movement of the kinetic component from S.O to S.D in the absence of the specific ligand or an absence of movement of the kinetic component to S.D even in the presence of inducers. Abnormalities of ER translocation have been identified in malignant tissues and found to be predominant among hormone therapy resistant ER+ breast cancers.

PROCEDURE A

Studying normal and abnormal translocation of the kinetic protein ER and sub-classification ER+ breast cancers on the basis of ER translocation.

Imprints are made from either fresh or cryopreserved (at −80C or lower temperature) breast cancer biopsies on to histological glass slides.

1. Replicates of tumor imprints are made on plain glass slides for examining the cellular location of ER as they exist in the tumor.
2. Replicates of tumor imprints are made on glass slides pre-coated with saline solution ( 0.9% Sodium Chloride in distilled water) and transferred to moisture chamber and kept at 37C for 30 minutes, to examine the effect of exposure to ligand-free saline solution at 37C.
4. Replicates of imprints are made on glass slides precoated with specific ligands to study their effect on ER translocation. (For pre-coating, saline solution of estrogen or DES (1–5 nanomolar concentration) are allowed to coat the entire surface of the glass slides and allowed to air dry) The imprints are incubated at 37C for 30 minutes in moisture chamber.
5. Replicates of imprints are made on glass slides precoated as described above, with 1–5 nanomolar solution of the drug Tamoxifen, to study its effect on tumor ER translocation and incubated at 37C for 30 minutes.
6. Replicates of imprints are made on glass slides pre-coated with solutions of control ligands (1–5 nanomolar concentrations of ORG 2058 or R5020 which are specific ligands for PR, but control ligands for ER); these slides help verify whether or not tumor ER translocation requires specific ligand.

All the slides are processed by ethanol dehydration-rehydration procedure as described under "Automation with Varistain" in the specification section of this report or manually, as described in prior publications (1,3,5–7,). This mode of tissue fixation is mandatory for detection of ER with the rabbit polyclonal (1–3,5–7) and monoclonal anti-ER antibody 1-F11 (19,20). Note: Ethanol dehydration rehydration procedure can be replaced with other modes of tissue fixation, previously found suitable for immunohistochemical detection of the kinetic component under scrutiny.

The fixed slides are washed in saline 3 times and incubated with rabbit polyclonal or monoclonal 1-F11 anti-ER antibody (ie: primary antibody) for 30 minutes at 37C in moisture chamber. Unbound antibody is removed by 3 saline washes and the cellular location of the antibody-bound ER is detected by one of the conventional staining procedures known to prior art : indirect immunofluorescence or immunoperoxidase procedure or biotin-avidin amplified immunofluorescent or immunoperoxidase procedure, or with the use of chemiluminescent probe labelled antibodies. For staining ER in tumor imprints, biotin-avidin immunoperoxidase technique was routinely employed (19,20). The slides were incubated for 30 minutes at room temperature, with biotin-labelled secondary antibodies (ie: anti-rabbit antibodies, if rabbit polyclonal anti-ER antibodies were employed as primary antibodies; anti-mouse immunoglobulins, if mouse monoclonal antibody 1-F11 was used as primary anti-ER antibody). After washing 3 times in saline to remove the excess secondary antibodies, the slides are incubated for 30 minutes with Avidin which is labelled with either fluorescein or chemiluminescent probe (immunoflourescent detection) or enzymes (eg: immunoperoxidase (19,20).

Detection of fluorescence is done UV microscope after removing the excess Avidin reagent by three sline washes. When enzyme labelled Avidin is used, the slides after washing in saline 3 times, are soaked in substrate buffer (0.1 M TRIS, pH 7.6 ) for 5 minutes, followed by five minutes in the substrate solution (DAB for peroxidase) to allow color development, and counter stained for 5–8 minutes with 1% Methyl Green solution (purchased from Kirkegaard and Perry Laboratories ). Excess Methyl Green is washed off by rinsing the slides quickly through 90% (2X), absolute ethanol (3X) and Xylene (2X). The slides are mounted with Permount and viewed under the light microscope for brown stain indicative of peroxidase activity. Color development is different, dependent upon the enzyme and the substrate system chosen for immunodetection.

For each tissue specimen, an antibody-negative control is prepared as follows: One of the replicates of slides with the imprint, crysection or cell is exposed to 1 mg/ml gelatin solution made in saline instead of the primary antibody. These slides are subsequently processed identical to other slides as described above. Any staining observed in these slides is to be interpreted as non-immunospecific and therefore caused by secondary reagents. These antibody control slides should be negative before the staining in other slides processed with the primary antibody is accepted as antibody specific or immunospecific staining.

Recording of Results:

The stained slides are examined microscopically and percent tumor cells in which the immunospecific staining is exclusively cytoplasmic (C+N−), both cytoplasmic and nuclear (C+N+), or exclusively nuclear (C−N+) are recorded either manually or with the aid of any commercially available protocols for computerised image analysis systems. Tumors in which no immunospecific staining is seen are recorded as ER(−) tumors.

Following the protocol detailed in Background section of the specification and as published previously (6,7), the ER+ tumors are subclassified as either TR+L ( with normal, ligand mediated translocation), TR+NL (with abnormal, non-ligand mediated translocation ) or TR(−) (abnormal, with no evidence of translocation). This subclassification step is accomplished either manually or with the aid of computerised image analyser.

Briefly, the basis for tumor sub-classification is as follows:

TR+L: In the absence of the specific ligand the staining is cytoplasmic (C+N−); Only in tissues on the ligand coated slides, the staining is either C+N+ or C−N+ among >30% of stained (ER+) cells. The tumor cell ER is normal requiring specific ligand binding for its transformation and translocation to the nucleus and nuclear binding.

TR+NL: In all the tumor cells incubated at 37° C., immunospecific staining is either C+N+ or C−N+ among ≧30% of stained (ER+) tumor cells. The tumor cell ER is abnormal because translocation and nuclear binding occurs in the absence of specific ligand.

TR(−): In all the slides, the immunospecific staining is C+N− among ≧70% of ER+ cells. ER is abnormal because it is unable to either transform or translocate and bind to the nucleus.

Interpretation of results and rationale:

Method for prediction of clinical response to hormone therapy for evaluating the value of this mode of subclassification in prospective clinical trials:

The mode of prediction is based on the correlative results obtained in the pilot study of retrospective analysis of 25 patients treated with hormone therapy (7). The primary tumors of these patients were among the 88 ER+tumors subclassified as TR+L, TR(−) or TR+NL (6,7), employing polyclonal anti-ER antibodies and immunofluorescent detection technique. When the tumors recurred or metastasied after surgical removal of the primaries (as was the normal clinical practice), these patients were treated with hormone therapy (7). Current practice is to treat immediately after surgery.

TR+L : Tumors in this subgroup are predicted to respond to hormone therapy (5/6 patients in this category responded in the pilot study). Specific ligand is essential for ER to translocate and bind to the ER specific sites in the tumor cell nucleus. Hormone therapy, either estrogen deprivation (eg: surgical or chemical oophorectomy), or oral intake of antiestrogen Tamoxifen is predicted to be an effective treatment in these tumors because, ER in the absence of estrogen or blocked by antiestrogen, is unable to execute its biological function. The tumor is unable to grow.

TR+NL: Tumors in this subgroup are predicted to fail hormonal treatment because ER is able to bind to the nucleus even in the absence of specific ligand. Either estrogen deprivation or antiestrogen blockers will not affect the ability of this tumor ER to execute its function and therefore the cells will continue to grow under these conditions. Ten out of ten patients with TR+NL tumors failed to respond to hormone therapy.

TR(−): Tumors in this subgroup are likely to fail hormone therapy. Six out of nine patients in this category failed to respond to hormone treatment (7). ER, although can bind the specific ligand, is unable to translocate and bind to the tumor cell nucleus. In the absence of normally functioning ER, the tumor cells continue to grow. Therefore, neither estrogen deprivation, nor antiestrogen block aborts the tumor growth.

Quality Assurance Procedures: Inter-assay variability, inter-assesor consistency in sub-grouping, are performed as described in detail (6) to maintain high quality of performance. Automation of the procedural steps and computerization of data collection (computerized image analysis) ensure high degree of reproducibility. Use of staining procedures such as immunoperoxidase staining, allows storage of slides for extended period, repeat review of slides if necessary.

For objective evaluation of the predictive significance of this subgrouping via clinical trials, following parameters are to be recorded for each tumor. When clinical responses are ready and available, correlation between various subgroups and clinical response, correlation between predicted clinical outcome with the observed clinical results are determined. Statistical significance of the correlative data are calculated as described for retrospective analysis (7).

Recording Results of Immunohistochemical nuclear binding test:

Patient's I.D:

Menopausal Status: post-menopausal (natural or surgical

1.ER Status : + or (−)

2.ER Subgroup:
  TR+L (% cells with TR+L ER)
  TR+NL (% cells with TR+NL ER)
  TR(−) (% cells with TR(−) ER)

3.Statement of prediction on response to hormone therapy.

Procedure for identifying abnormalities in kinetic components other than steroid hormone receptors:

Illustrative example: Identification of abnormalities in the translocation from cytoplasmic transcription factors associated with interferon alpha response to the cell nucleus.

Interferon alpha is known to prevent virus entry into normal healthy cells. Interferon alpha therapy therefore became popular for certain types of cancers. Not all tumors responded to this therapy. Recent advances in technology has revealed that a kinetic protein, the transcription factor TF (also called ISGF3 or interferon stimulated growth factor)) is important for the functioning of interferon alpha to prevent virus entry into the cell (21). Immunohistochemical test described in this invention will be useful for identifying the abnormalities in the translocation of TF which will render the cells unresponsive to interferon alpha. In the normal cell, the enzyme Tyrosine kinase associated with the cell surface interferon alpha receptor is activated when the interferon (ligand) binds to its receptor. The activated enzyme phosphorylates the cytoplasmic TF. Phosphorylated TF then translocates to the cell nuclei where it binds to interferon-responsive nuclear sites. Any defect either in the interferon receptor, its Tyrosine kinase, or mutation in the TF will manifest itself as a translocation abnormality of TF: inability of TF to translocate to the nucleus; or translocation of TF in the absence of interferon binding to its receptor. In either case, the cell will be unresponsive to interferon therapy.

Procedural steps to identify whether or not TF shows normal or abnormal transclocation in the malignant tissue, are identical to the those described above for ER, with the following modifications:

Interferon alpha serves as the specific ligand for coating ligand coated slides. Interferon beta serves as the control ligand. Imprints of tumors to be examined are made on these slides. Cell smears from normal body fluids, made on ligand coated and control ligand coated slides serve as a reference standard for demonstrating normal kinetics of TF in non malignant cells. Polyclonal antibodies to TF which are capable of reacting with unphosphorylated and phosphororylated forms of TF whether it is cytoplasmic or bound to the cell nuclei are used to the location of TF (Anti-TF described by Chris Schindler et al as referenced in the publication by Jean Marx (21).

The processing of the slides after ligand incubation step is identical to what is described for ER. The sub-classification of TF+ cells is done similarly and the groups are TR+L (normal, showing translocation only in interferon-alpha coated slides), TR+NL (abnormal, translocating to the nucleus in the absence of ligand) and TR(−) (abnormal, showing no translocation).

PROCEDURE B

Application of immunohistochemical test for first level screening of drugs in order to select those which have the capcity to alter the intra-cellular translocation of kinetic components found in malignancies.

Definitions: A drug is a pharmaceutical compound; a component of an extract of a biological source; a synthetic polypeptide, a polynucleotide, a mineral, metal, a nucleic acid, a carbohydrate or a lipid. A drug binds to any site present either on the kinetic component or on cellular factors which are necessary for the translocation of the kinetic component and thereby either inhibits the translocation process, or alters the abnormal patterns of translocation exhibited by the kinetic component.

The term "Pilot drug screening" refers to the process of examining an array of several drugs to detect which ones among them, when used in the immuno-histochemical assay system show evidence of inhibiting or altering the translocation process of the kinetic component under study. The term "pilot screening" does not include the process of proving the efficacy of the drug as a therapeutic drug via in-vivo experiments and clinical testing.

Procedural modifications consistent with the use of immunohistochemical test as a drug screening test include the following:

a) In addition to the specific ligand coated and control ligand coated slides, slides coated with the solution of the drug/s to be tested are included.

b) Imprints of tumors pre-tested and found to contain normal or abnormal variety of translocation are made on each one of the drugs and the results compared.

c) Either cryosections of normal tissues which contain the kinetic component or cell smears made from normal body fluids serve as reference standards to study effect of the drug on translocation of kinetic component expressed by normal tissues. To achieve this purpose, cryosections are thaw mounted or cell smears are made on drug coated slides and on plain glass slides for comparison.

The incubation steps, tissue fixation, primary and secondary antibody application, immunostaining, sub-grouping, data collection are identical to those decribed previously for Procedure A.

Interpretation of results and criteria for drug selection:

a) In the TR(−) tumor imprints, (but not in the normal tissue samples) an identification of C+N+ or C−N+ immunostaining in >50% of ER+ cells only in the drug coated slides is an indication of drug induced in-vitro translocation of otherwise non-translocating ER. Absence of such an effect in normal tissues indicates that the drug alters only the defective TR(−) variety of ER found in malignancy. This drug is therefore selected for additional scrutiny for in-vivo studies.

b) In the TR+NL tumor imprinted on the drug-coated slides, an observation of C+N− immunospecific staining among >50% of stained cells is indicative of inhibition of abnormal nuclear binding by the drug. This drug is therefore selected for evaluating its effect on normal ligand induced nuclear binding. This is accomplished by imprinting TR+L tumors on slides coated with a mixture of the drug and specific ligand solution, in addition to the ligand coated and control ligand coated slides which are routinely included in the procedure. On comparative analysis of results, a predominance of C+N+ and C−N+ staining in all the ligand coated slides (whether or not drug was also present) is indicative of exclusivity of the drug's inhibitory effect to the abnormal nuclear binding only. This drug is therefore selected for further in-vivo testing. Instead, a presence of predominant C+N− staining in tumor imprinted on the "drug plus ligand" slides demonstrates an inhibition of even normal nuclear binding by the drug. This drug is therefore likely to be toxic to the normal cells. Table 3 illustrates these points of interpretation succintly.

TABLE 3

| Reference Std:Type | (−) Ligand | (+) Ligand | (+) drug | +Both Ligand and Drug |
|---|---|---|---|---|
| TR(−) | C+N− | C+N− | C+N+,C−N+ | C+N+,C−N+ |
| TR+NL | C+N+,C−N+ | C+N+,C−N+ | C+N− | C+N− |
| TR+NL | C+N− | C−N+ | C+N− | C−N+ |

Note: Normal type of translocation is unaffected, while the abnormal types are altered in the presence of the drug. This type of staining in the presence of the drug, even when either one of the two abnormal types of translocation are altered, the drug is to be selected for additional in-vivo studies.

PROCEDURE C

Application of immunohistochemical test to identify the presence of components (toxins) in drinking water, food extracts, solutions of non-prescription drugs, food dyes, serum or plasma collected from individuals. Definition of a Toxin: "Toxin" as specified with reference to the kinetic substances, is a component which is capable of interacting with the normal kinetic substance and inhibiting its normal ligand mediated translocation from S.O to S.D. For example, with reference to ER, its ligand mediated nuclear binding is prevented. Alternately, the toxin, is a component which promotes the translocation of a kinetic component in the absence of its specific ligand, thus coverting TR+L to TR+NL variety. Definition of "Toxin Screening" as specified in this report, is restricted to the process of identification of the presence of a component in the test sample which is detrimental to the normal translocation of kinetic substances. The definition does not include the process of identifying which component is the toxin. Preliminary screening as described below is the initial step towards the identification and purification of the toxin.

Procedural modifications are identical to those described for drug screening but the end point is different. The desirable effect of a drug is its capacity to affecting the abnormal while a toxin identified by its ability to alter the normal to abnormal. Instead of drug coated slides, the solutions or body fluids to be examined for the presence of "toxins" are coated on the slides. The TR+L variety of tumor is imprinted or normal cells are smeared on these slides, along with the experimental set of slides described for procedure A. In addition, another slide is precoated with a mixture of ligand and the solution to be tested for toxin. The TR+L tumor imprinted or normal cells smeared on this slide as well. Incubations, fixation, immunostaining and sub-grouping steps are performed as described for Procedure A.

Criteria for labelling a sample as containing "a toxin" are the following: a) Presence of C+N− staining among >50% of ER+ normal cells or the reference tumor of TR+L type in the presence of a mixture of specific ligand and the solution being tested, is indicative of inhibition of normal ligand mediated translocation by the toxin. b) The presence of C+N+ or C−N+staining in normal cell smears or TR+L tumor imprints on slides coated only with the solution being tested for toxins is indicative of induction of translocation in the absence of specific ligand. In either of the situations described above, the the solution is said to contain a component which affects the translocation pattern and is therefore selected for additional verification by in-vivo culture studies.

Identification of the toxin-positive sample by first level screening is an initial step essential for purification of the toxic components.

PROCEDURE D

Application of immunohistochemical procedure for hybridoma screening.

Definition: Hybridoma screening as specified in this report refers to the selection of monoclonal hybridomas which secrete anti-ER antibodies with unique features: broad spectrum reactivity with both cytoplasmic and nuclear ER, ligand complexed or uncomplexed; or narrow spectrum antibodies which are specific to only defective ER of TR(−) variety; or to TR+NL variety. Broad spectrum antibodies are essential for use in immunohistochemical procedures utilized for sub-classifying kinetic components on the basis of translocation abnormalities. Thus, hybridoma screening does not refer to production of hybrids and selection of clones by sub-cloning, nor to the differential selection of antibody secretors from non-secretors.

Immunohistochemical procedure was successfully employed to screen and select a hybridoma which secretes monoclonal anti-ER antibody molecules, as described in prior publications (19,20). The unique feature of this antibody designated 20-F8-1-G7-1-F11 (abbreviated 1-F11) for which it was selected, is its ability to bind specifically to cytoplasmic ER, uncomplexed or complexed with the specific ligand and with the uncomplexed or ligand complexed nuclear bound ER equally well (19,20). In this respect, 1-F11, although monoclonal, is similar to the rabbit polyclonal anti-ER antibody which was the primary antibody in the immunohistochemical procedure to sub-group ER+ tumors (5,6,7), and as reference antibody for screening 1-F11. This unique feature is attributed to the fact that the epitope in the ER molecule which is recognized by 1-F11 is unaffected by ligand binding, transformation and nuclear binding of ER and therefore always antibody-accessible.

The specificity of 1-F11 antibodies to ER and only ER was documented by a variety of standard procedures known to prior art :

1) demonstration of ability to complex with radio-ligand bound ER by sucrose density gradient centrifugation and by non-denaturing acrylamide gel electrophoresis;
2) Immuno-blotting procedures to ascertain antibody recognition of:
   a) unreduced, undenatured ER complexed with radio-labelled ligand,
   b) unreduced, SDS denatured ER uncomplexed with ligand,
   c) reduced, SDS denatured cytosolic ER derived from human breast tumors;
3) Immunoblotting procedures to document:
   an absence of reactivity with cytosolic proteins derived from ER negative tumors;
   recognition of a single 65–69 kilodalton protein in the reduced and SDS denatured cytosol of ER+ lamb uterine tissue and of MCF-7 cells;
   Identification of a single 65–69 K protein in the reduced SDS extracted antigen, dissociated from 1-F11antibody-sepharose beads reacted with crude extracts of lamb uterus.
4) Immunohistochemical procedures to show the antibody recognition of un-liganded, or ligand complexed cytosolic and nuclear ER of MCF-7 cells and to demonstrate ligand mediated translocation of ER in them.
5) Immunohistochemical procedure to document the utility of 1-F11 antibody to identify defective ER among the cell lines of human origin: MCF-7 cells were found to contain predominantly of TR+L variety of ER with polyclonal anti-ER antibodies and with 1-F11 monoclonal anti-ER antibody; anti-estrogen resistant cell line, LY-2 was found to contain TR(−) variety of defective ER with the use of polyclonal antibodies, as with 1-F11 antibody.
6) Immunohistochemical procedure to demonstrate the utility of 1-F11 antibody, to sub-classify the ER+ breast tumors, as defective TR (−) or TR+NL or normal TR+L.

The screening of hybridoma supernates (diluted 6X or 1OX) at the first and second level cloning resulted in the identification of 20-F8-1-G7 hybrid and subsequent selection of the final clone of 20-F8-1-G7-1-F11 hybridoma (monoclonal with IgG-1 isotype) as a broad spectrum anti-ER antibody secretor was achieved in the following manner as described in the abstracts (19,20). The hybridoma supernates, free of dyes were reacted with 5 micron sections of several paraffin embedded ER+ human breast tumors and ER(−) tumors and antibody binding verified by biotin-avidin amplified immunoperoxidase staining. Those hybridoma supernates which were non-reactive with ER(−) tumors but were immunoreactive with all ER+ tumors were further examined for their recognition of cytosolic ER complexed with radioactive estradiol with biochemical procedures and selected if positive, for final cloning. The secretory product of the final clones (1-F11 is an example) was additionally scrutinised for its monospecificity to ER, its capacity to react with and bind to ligand-free, ligand bound, cytosolic and nuclear-bound ER by a variety of biochemical and immunohistochemical procedures outlined above. The antibodies were also verified for their capacity to recognize ER in the cryosections or in the imprints of TR+L, TR+NL and TR(−) sub-classes of ER+ tumors when tested by immunohistochemical (Procedure A ) and by biochemical procedures.

Procedural steps for screening hybridomas: Selection of broad spectrum versus narrow spectrum monoclonal antibodies.

1. Hybridoma culture medium containing the antibody secreted by monoclonal hybridomas are dialyzed in 0.1M TRIS-EDTA-Borate buffer (TEB), pH 8.0 to remove all the phenol red dye and other small molecules. Only dialyzed culture supernates are utilized for screening.
2. Employing steps described in Procedure A, one set of coated slides are to be prepared for each culture supernate to be evaluated.
3. Tumor imprints are made from tumors which were pre-tested employing polyclonal anti-ER antibody and classified as TR+L ( 90% of the tumor cells showing TR+L variety of ER).
4. After ligand incubation and fixation steps, one set of slides are to be incubated with the reference antibody (polyclonal anti-ER antibody); each of other sets should receive one of the hybridoma culture supernates.
5. The immunostaining procedure and data collection is the same as described for Procedure A.
6. Those culture supernates which yield results identical to the reference antibody are selected as broad spectrum antibodies. These will stain cytoplasmic ER in slides without the specific ligand and nuclear bound ER in the ligand coated slides.

Note:
1) Instead of tumor imprints, cultured cell lines known to be uniformly TR+L and grown on histological slides are also suitable for hybridoma screening. Specific Ligand or control ligand is introduced in the growth medium as described previously for MCF-7 cells (3). Slides are to be thoroughly washed free of phenol red prior to incubation with the hybridoma culture supernate. Immunohistochemical staining steps and data collection are as described for Procedure A.
2) Identification of TR(−) specific or TR+NL specific hybridomas is by repeating the procedure with either imprints of tumors with these type of defects or cultured cells pre-tested to contain one of those defective types of ER. Hybridoma culture supernates which stain only the TR(−) or TR+NL tumors or cell lines are chosen as narrow spectrum antibodies.

The selected hybridomas are expanded in tissue culture or ascites employing standard hybridoma technology known to prior art. Their secretory products are re-evaluated for monospecificity to ER, by employing procedures described above for 1-F11 or as consolidated in the book "Immunology of Steroid Hormone Receptors Vol I: Estrogen Receptors" (22).

SCOPE OF THE IMMUNOHISTOCHEMICAL PROCEDURE

Although this invention is disclosed with reference to particular embodiment, the principles involved are susceptible for use in numerous other embodiments which will be apparent to persons skilled in art. A few of those embodiments are outlined below to demonstrate the scope of this invention. The invention however is to be limited only as indicated by the scope of the appended claims.

1. The immunohistochemical procedure described is the most economical way to detect the presence of translocation defects in a kinetic component. Prior knowledge of what causes the translocation defect or the exact location of the defect are not necessary. What is required is a broad spectrum antibody, either poly or monoclonal, which reacts with both the normal and defective kinetic component. Therefore, an immunohistochemical staining kit can be devised containing the embodiments of this procedure for detecting translocation defects of kinetic component.
2. Either the polyclonal anti-ER antibodies (1–3, 5–7) or monoclonal anti-ER antibodies designated 1-F11, may be used in a kit either as a whole molecule, as Fab fragments which retain the antibody's unique characterisitics, or as genetically engineered antibody fragment with identical properties, for predicting which among ER+ malignancies are clinically susceptible to hormone therapies and which will be resistant to such therapies. Thus, these antibodies or their biologically active fragments may be supplied in a kit designed as predictive kit for cancers of the breast, endometrium, prostate or cancers of the nervous system and of those tissues which are ER+ and hormone therapy is offered as a treatment modality.
3. The embodiments of this procedure may be included in a kit for sub-classification of ER+ malignancies, a kit to screen for drugs which may have potential use to treat those malignancies, or a kit intended for both subclassificaton of tumors and for drug screening. This procedure offers a convenient method for simultaneous screening of ER+ malignancies for defective and non-defective ER and for customising a most effective drug treatment for each tumor. Testing the efficacy of the drug to alter the nuclear binding of ER in each tumor can be achieved with this method.
4. The embodiments of this procedure may be included in a kit for use in the identification of toxins in food, drinks, drinking water or in non-prescription drugs, since this procedure offers an economical method for screening for toxins which affect the translocation process of kinetic components, including steroid hormone receptors.
5. The embodiments of this procedure may be included in a kit for hybridoma screening because this procedure is useful for selecting hybridomas which secrete broad spectrum antibodies specific to any kinetic component (example: Interferon induced translocation of transfer factors) or cellular factors related to kinetic components which are capable of interacting with and binding to a kinetic component whether it is ligand free, or ligand bound; whether it is present in S.O or as bound to S.D.
6. The immunohistochemical procedure can be applied to identify whether or not a newly discovered gene product is a kinetic component; if it is, to define inhibitors and inducers of its intracellular translocation; to detect abnormalities of translocation in diseased tissues in which the component is present.
7. With the described procedure, the individual chromosomes to which a nuclear binding component binds, can easily be identified; abnormalities in chromosome binding of the component detected. Diseases in which erroneous binding of a regulatory protein to a 'wrong' chromosome or to a wrong location in the 'right' chromosome can easily be identified with the use of cells which are programmed to enter the growth phase.
7. The immunohistochemical procedure should become an excellent tool for molecular biologists and biochemists who are investigating gene regulation and signal transduction. Identification of transcription factors which are essential for transcribing a newly discovered regulatory pathway or a gene product, is an expensive multistep process, with biochemical or molecular cloning approaches. Applying the immunohistochemical procedure as described, equipped with a broad spectrum antibody to a kinetic regulatory protein, a straight forward identification of defects in its translocation are identified first. Next, a comparison of structural components of a normal translocator versus defective non-translocator will provide a clue regarding those transcription factors which are essential to induce intracellular translocation of a nuclear binding component.

What I claim is:

1. An immunohistochemical method to detect normal and abnormal intracellular movement of a kinetic cellular component from one cellular compartment to another, comprising the steps of:

a) pre-coating the glass slides with a solution containing a ligand specific to the kinetic component to be examined, a control ligand or no ligand;

wherein a specific ligand is an agent or a compound which upon incubation with the said kinetic component effects its intracellular movement from one compartment to another;

wherein a control ligand does not upon incubation effect an intracellular movement of the said kinetic component;

b) imprinting tumor tissue, thaw mounting cryosections of normal or tumor tissue or smearing core-needle biopsies or cell suspensions on uncoated or said pre-coated glass slides;

c) incubating the slides in moist chamber to allow for ligand binding;

d) fixing the incubated tissue;

e) detecting the kinetic component by binding an antibody to the said kinetic component;

f) determining the normal or abnormal movement of the said kinetic component by comparing its cellular location when incubated with or without the specific ligand.

2. The immunohistochemical method of claim 1 whereby breast tumors are classified based upon the presence in tumor cells of normal or defective estrogen receptors, wherein, estrogen receptor is the kinetic component;

wherein, normal estrogen receptor upon incubation with estrogen receptor-specific ligand moves from the cytoplasm to the nuclear compartment of the cell and the tumor with said normal receptors is classified as Tr+L;

wherein, defective estrogen receptor upon incubation with estrogen receptor-specific ligand fails to move from cytoplasm to the nuclear compartment of the cell and the tumor with said defective estroegen receptors are classified as Tr(−);

wherein, defective estrogen receptors upon incubation with no ligand or with control ligand moves from the cytoplasm to the nuclear compartment of the cell and the tumor with said defective estrogen receptors is classified as Tr+NL;

wherein, the detection of normal and defective estrogen receptor is accomplished by:

a) imprinting tumor tissue, thaw mounting cryosections of tumor or normal tissue, smearing core-needle biopsy or cell suspension on estrogen receptor-specific ligand coated or control ligand coated slides;

b) incubating the slides in moist chamber to allow ligand binding;

c) fixing the incubated tissue;

d) detecting the estrogen receptor by binding an antibody to estrogen receptor;

e) determining the percentage of cells with normal or defective estrogen receptors and classifying as normal or Tr+L, defective or Tr(−), or as defective or TR+NL variety.

3. The immunohistochemical method of claim 2 whereby breast tumor patients are selected for hormonal or other non-hormonal modes of treatments;

wherein patients with tumors of Tr+L variety containing normal estrogen receptors are predicted to be responders to hormonal therapy and thereby selected for hormonal treatments;

wherein patients with tumors of Tr(−) and /or Tr+NL varieties containing defective estrogen receptors are predicted to be non-responsive to hormonal modes of therapy and thereby selected for non-hormonal modes of therapies.

4. An immunohistochemical method of screening for the ligand specific for a kinetic cellular component wherein a specific ligand is an agent or a compound that upon incubation with the kinetic cellular component effects its intracellular movement from one compartment to another;

wherein estrogen receptor is a kinetic cellular component and specific ligand upon incubation effects the movement of estrogen receptor from the cytoplasm to the nuclear compartment of the cell ligand screening comprise the steps of:

a) precoating glass slides with a solution of ligand known to be specific to estrogen receptor, the solution to be screened for the presence of a specific ligand or a solution of control ligand;

b) imprinting tumor tissue with normal estrogen receptor, thaw-mounting cryosections of tumor or normal tissue with estrogen receptor, smearing cell suspension from estrogen receptor containing tissue onto said pre-coated slides;

c) incubating the slides in a moist chamber to allow ligand binding;

d) fixing the incubated tissue;

e) detecting the estrogen receptor by binding an antibody specific to estrogen receptor;

f) determining the cellular location of estrogen receptor in the presence vs absence of the solution being screened for ligand.

5. The immunohistochemical ligand screening method of claim 4, whereby screening for an inhibitor-ligand is accomplished, wherein an inhibitor-ligand is an agent or a compound which when combined with an estrogen receptor specific ligand, prevents the estrogen receptor from moving from the cytoplasm to the nuclear compartment of the cell;

and the method of screening further comprising the steps of:

a) precoating glass slides with a solution containing estrogen receptor specific ligand, a solution of control ligand or a solution of specific ligand mixed with the solution to be screened for an inhibitor-ligand;

b) following steps b-e specified for claim 4;

c) determining the location of estrogen receptor in the presence of specific ligand and in the mixture containing both the specific ligand and the ligand being examined.

6. An immunohistochemical method for screening for monoclonal anti-estrogen receptor antibodies with exclusive specificity for either normal Tr+L, defective Tr(−) or defective Tr+NL estrogen receptors, wherein to normal/Tr+L receptors are those which need binding to the specific ligand to move from cytoplasm to the nuclear compartment of the cell;

wherein defective Tr(−) estrogen receptors are those which do not move from cytoplasm to the nuclear compartment even upon binding to estrogen receptor specific ligand;

wherein defective Tr+NL estrogen receptors are those which will move from cytoplasm to nuclear compartment of the cell even in the absence of estrogen receptor specific ligand;

wherein the antibody screening comprises the steps of:
        a) imprinting on glass slide, or thaw mounting cryosections of normal tissue or tumor tissue with Tr+L estrogen receptors, Tr(−) estrogen b) air drying the tissue followed by fixing the tissue on the slide;

c) contacting the fixed tissue with solution containing monoclonal antiestrogen receptor antibody;

d) determining the antibody binding to Tr+L, Tr(−) or Tr+NL estrogen receptors or to all three by immunohistochemical staining techniques.

7. A kit intended for the purpose as described in claim 1 and comprising any of the following either singly or in combination a) Ligand-coated glass slides b) saline or buffer-coated glass slides c) tissue or tumor imprinted glass slides d) glass slides smeared with cell suspensions e) instructions with procedural details described in claim 1.

* * * * *

UNITED STATES PATENT AND TRADEMARK OFFICE
CERTIFICATE OF CORRECTION

PATENT NO. : 6,162,606
DATED : December 19, 2000
INVENTOR(S) : Shanthi Raam

Page 1 of 2

It is certified that error appears in the above-identified patent and that said Letters Patent is hereby corrected as shown below:

Title page, item [75],
Inventor: Shanthi Raam, replace with current address:
36 Woodland Way, Rehoboth, MA 02769

Column 1,
Insert "Govt. Interest Grant No: RO1-NIH-CA37499"
Other Publications: Reference 3-, change "Ram to Raam"

Title page,
Other Publications: Change "Fugua" to "Fuqua"

Column 7,
Line 3, change "completed" to --complexed--
Line 7, delete "6"
Line 18, change "completed" to --complexed--
Line 44, change "Occur" to --occurs--

Column 12,
Line 38, change "are" to --were--
Line 42, after the word "done" insert --with--

UNITED STATES PATENT AND TRADEMARK OFFICE
CERTIFICATE OF CORRECTION

PATENT NO. : 6,162,606
DATED : December 19, 200
INVENTOR(S) : Shanthi Raam

It is certified that error appears in the above-identified patent and that said Letters Patent is hereby corrected as shown below:

Column 15,
Line 10, replace "to" with --for--
Line 24, change "capcity" to --capacity--

Column 16,
Line 37, table 3, line 3, change "TR+NL" to --TR+L--

Column 23,
Line 19, add "receptors or TR-NL estrogen receptors", after "estrogen"

Signed and Sealed this

Third Day of July, 2001

*Attest:*

NICHOLAS P. GODICI
*Attesting Officer*     *Acting Director of the United States Patent and Trademark Office*